United States Patent [19]

Peters et al.

[11] Patent Number: Plant 5,586

[45] Date of Patent: Dec. 3, 1985

[54] NECTARINE TREE, "STAR BRITE"

[76] Inventors: Richard Peters, 4854 E. Butler Ave.; Eric Wuhl, 5480 E. Lane St., both of Fresno, Calif. 93727

[21] Appl. No.: 585,266

[22] Filed: Mar. 1, 1984

[51] Int. Cl.[4] ..... A01H 5/03

[52] U.S. Cl. ..... Plt./41

[58] Field of Search ..... Plt./41

*Primary Examiner*—Robert E. Bagwill

*Attorney, Agent, or Firm*—Worrel & Worrel

[57] ABSTRACT

A new and distinctive variety of nectarine tree which produces freestone fruit which are most closely similar to the fruit of the May Grand Nectarine Tree of U.S. Plant Pat. No. 2,794 but which ripens five days or so earlier and is distinguished therefrom by being larger, redder and somewhat more pointed.

1 Drawing Figure

BACKGROUND OF THE NEW VARIETY

The present invention relates to a new and distinct variety of nectarine tree, known as "STAR BRITE", and more particularly to such a nectarine tree which is most closely similar to the May Grand Nectarine Tree, U.S. Plant Pat. No. 2,794, but from which it is distinguished by bearing fruit which is larger, redder, more pointed, and which ripens on the average approximately five days earlier than the May Grand, grown under substantially the same cultural conditions.

For many years, the applicants have engaged in the commercial production of deciduous fruit. An important part of such commercial operation has been the continuous search for improved varieties so as to improve the production and the quality of the varieties of the fruit produced.

ORIGIN

The nectarine tree of the present invention was discovered by the applicants, Eric Wuhl and Richard Peters, in June of 1977 growing as a sport on an Early Sungrand Nectarine Tree, unpatented, in a commercial orchard of Early Sungrand Nectarine Trees on the East Side Ranch at 16405 East Goodfellow, Sanger, Calif., then owned by a partnership consisting of Richard Peters and CLW and Associates, a New Jersey Corporation.

ASEXUAL REPRODUCTION

The applicants, Eric Wuhl and Richard Peters, asexually reproduced the subject variety by budding it into various rootstock at the East Side Ranch and observed its characteristics over a period of five or six years. The asexually reproduced progeny of the subject variety nectarine tree displayed the same characteristics as the original sport discovered by the applicants in June of 1977. Of the nectarine trees known to the applicants, the subject variety is most nearly similar to the May Grand Nectarine Tree of U.S. Plant Pat. No. 2,794, but is distinguished therefrom by producing fruit which are larger, redder, somewhat more pointed, and which ripens on an average of five days earlier.

BRIEF DESCRIPTION OF THE DRAWING

The drawing is an illustration, by photographic reproduction in color, of a twig of the subject variety of nectarine tree with representative leaves thereon, three whole nectarines of the subject variety and one halved nectarine showing the internal flesh color.

BOTANICAL DETAILS

The botanical details of the new and distinct variety of nectarine tree comprising the subject matter of this application are as follows, the color terminology is in accordance with the *Dictionary of Color,* by Maerz and Paul of McGraw-Hill Book Company, Inc. of New York, N.Y., Second Edition, 1950.

TREE

Size: Large.
Figure: Spreading.
Productivity: Very productive.
Regularity of bearing: Regular bearing.
Trunk:
- *Diameter in relation to length.*—Stocky.
- *Surface characteristics.*—Medium.

Branches:
- *Size.*—Medium.
- *Surface character.*—Medium.
- *Color.*—Vandyke Brown, Page 37, Plate 7, A-11.
- *Lenticels.*—Numerous, average size 1×5 mm.

Leaves:
- *Size.*—Large.
- *Length.*—180 mm.
- *Width.*—47 mm.
- *Shape.*—Oval-Lanceolate.
- *Color.*—Upperside — Polo Green, Page 69, Plate 23, 1-9; Lowerside — Cypress Green to Forest Green, Page 69, Plate 23, J-7.
- *Marginal form.*—Finely serrate.
- *Petiole.*—Length 15 mm; thickness 2 mm.
- *Stem glands.*—Number 1-3; alternate; 0.3×0.5 mm; globose and reniform; goldish green in color.

Flower buds:
- *Size.*—Large.
- *Shape.*—Obtuse and plump.
- *Surface.*—Pubescent.

Flowers:
- *Dates of bloom.*—First bloom — Feb. 14 in 1983; Full bloom — Feb. 23 in 1983.
- *Size.*—Large.
- *Color.*—Upperside: Peach-blossom, Page 25, Plate 1, C-3; Lowerside: Dolly Pink, Page 27, Plate 2, A-4.

*Number of pistils.*—One.
*Number of stamens.*—38 to 45.

FRUIT

Maturity: Met minimum maturity standards in Arvin, Calif. by June 1 in 1983.
Size:
*Uniformity.*—Uniform.
*Diameter.*—61 to 67 mm.
*Transverse in suture plane.*—60 to 64 mm.
*Transverse at right angles to suture plane.*—66 to 68 mm.
Form:
*Uniformity.*—Uniform.
*Shape.*—Round-oblong with equal sides and beaked, prolonged pistil point.
*Suture.*—Distinct, shallow; extends from base to pistil point.
*Ventral surface.*—Slightly lipped, deeper at apex and base than in the middle.
*Stem cavity.*—Acute, 15 mm×25 mm×8 mm deep.
*Base.*—Shoulders rounded.
*Apex.*—Cuspidate.
*Pistil point.*—Apical.
Stem:
*Length.*—10 mm.
*Caliper.*—4 mm.
Skin:
*Thickness.*—Medium.
*Texture.*—Medium.
*Tendency to crack.*—None.
*Color.*—Ground color: Navaho, Page 43, Plate 10, C-12; Blush: Algerian Red to Crimson Maple, Page 37, Plate 7, L-5.
*Pubescence.*—None.
Flesh:
*Color.*—Corn, Page 43, Plate 10, K-5.
*Color of pit well.*—Yellow Ochre, Page 45, Plate 11, L-7.

*Amygdalin.*—Slight.
*Juice.*—Abundant.
*Flavor.*—Slightly acid; semi-bland.
*Aroma.*—Distinct and pleasant.
*Texture.*—Medium and melting.
*Fibers.*—Few and fine.
Stone: Free.
*Size.*—Large, 40 to 42 mm long; 25 to 28 mm breadth; 21 to 22 mm thick.
*Form.*—Ovate and pointed.
*Sutures.*—Ventral: narrow, furrowed in middle; Dorsal: wide and lipped in the middle.
*Base.*—Straight.
*Apex.*—Acute.
*Sides.*—Irregularly furrowed near apex; pitted towards base.
*Color.*—Amber-glow, Page 47, Plate 12, H-10.
*Splitting tendency.*—None observed.
Use: Fresh market.
Keeping quality: Excellent.
Shipping quality: Good.

Although the new variety of nectarine tree possesses the described characteristics under the growing conditions prevailing in Fresno County, Calif., in the central portion of the San Joaquin Valley, it is to be understood that variations of the usual magnitude in characteristics incident to changes in growing conditions, fertilization, pruning and pest control are to be expected.

Having described our new variety of nectarine tree, what we claim as new and desire to secure by Plant Letters patent is:

1. A new and distinct variety of nectarine tree, substantially as illustrated and described, particularly characterized by its being most nearly similar to the May Grand Nectarine Tree of U.S. Plant Pat. No. 2,794, but from which it is distinguished by producing fruit which is larger, redder and which ripens five days earlier.

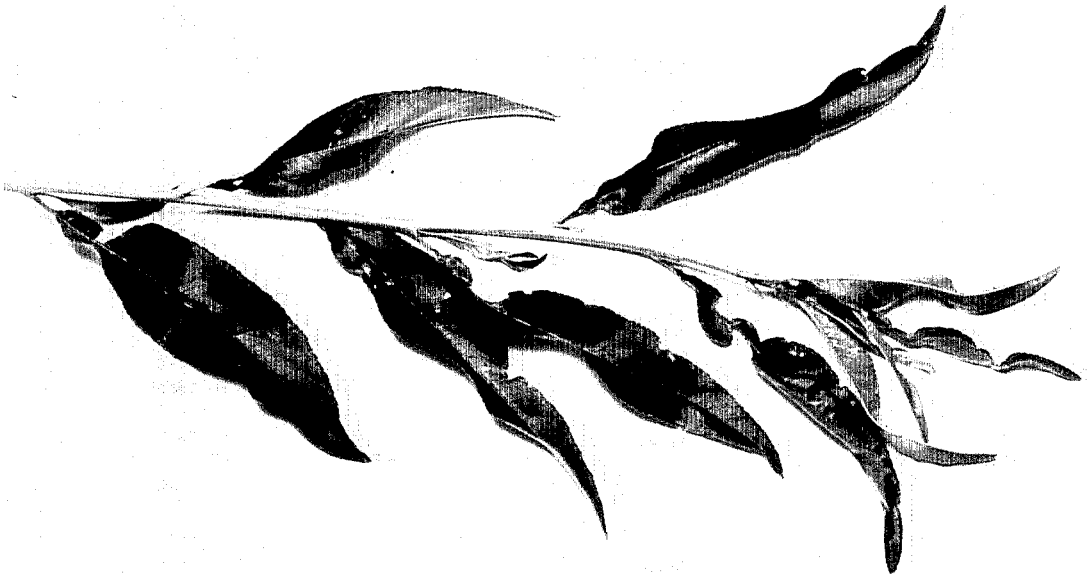
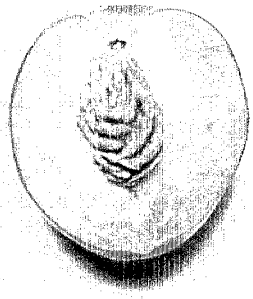
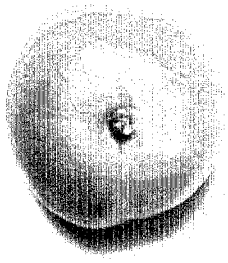
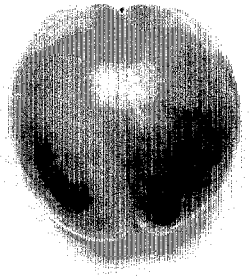
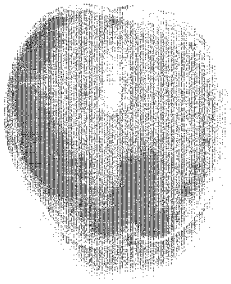

* * * * *